United States Patent [19]
Lucas et al.

[11] Patent Number: 6,027,879
[45] Date of Patent: Feb. 22, 2000

[54] DETECTION AND ISOLATION OF NUCLEIC ACID SEQUENCES USING A BIFUNCTIONAL HYBRIDIZATION PROBE

[75] Inventors: Joe N. Lucas, San Ramon; Tore Straume, Tracy; Kenneth T. Bogen, Walnut Creek, all of Calif.

[73] Assignee: The Regents of the University of California, Oakland, Calif.

[21] Appl. No.: 08/513,160

[22] Filed: Aug. 9, 1995

[51] Int. Cl.⁷ ..................................................... C12Q 1/68
[52] U.S. Cl. .............................. 435/6; 536/23.1; 536/243
[58] Field of Search .................................. 435/6, 5, 91.2, 435/183, 91.1; 536/23.1, 24.3, 24.33, 26.5; 935/76, 77

[56] References Cited

U.S. PATENT DOCUMENTS

| | | | |
|---|---|---|---|
| 4,358,535 | 11/1982 | Falkow et al. | |
| 4,376,110 | 3/1983 | David et al. | |
| 4,486,539 | 12/1984 | Ranki et al. | |
| 4,556,643 | 12/1985 | Paau et al. | |
| 4,563,419 | 1/1986 | Ranki et al. | |
| 4,794,082 | 12/1988 | Sigler. | |
| 5,118,792 | 6/1992 | Warren et al. | 530/350 |
| 5,210,015 | 5/1993 | Gelfand et al. | 435/6 |
| 5,232,829 | 8/1993 | Longiaru et al. | 435/6 |
| 5,273,882 | 12/1993 | Snitman et al. | |
| 5,380,833 | 1/1995 | Urdea | 536/22.1 |
| 5,387,505 | 2/1995 | Wu | 435/6 |
| 5,491,063 | 2/1996 | Fisher et al. | 435/6 |
| 5,510,475 | 4/1996 | Agrawal et al. | 536/24.3 |
| 5,571,677 | 11/1996 | Gryaznov | 436/6 |
| 5,616,465 | 4/1997 | Lucas et al. | 435/6 |
| 5,670,326 | 9/1997 | Beutel | 435/7.1 |
| 5,741,637 | 4/1998 | Rueget et al. | 435/6 |

FOREIGN PATENT DOCUMENTS

| | | |
|---|---|---|
| 0 079 139 | 11/1982 | European Pat. Off. . |
| 0 285 057 | 6/1983 | European Pat. Off. . |
| 0 286 898 | 6/1983 | European Pat. Off. . |
| 0 117 440 | 1/1984 | European Pat. Off. . |
| 0 231 495 | 12/1986 | European Pat. Off. . |
| 0 235 726 | 2/1987 | European Pat. Off. . |
| 0 292 128 | 4/1988 | European Pat. Off. . |
| WO 83/01459 | 4/1983 | WIPO . |
| WO 84/03285 | 8/1984 | WIPO . |
| WO 85/04674 | 10/1985 | WIPO . |
| WO 87/03622 | 6/1987 | WIPO . |
| WO 87/03911 | 7/1987 | WIPO . |
| WO 88/01302 | 2/1988 | WIPO . |

OTHER PUBLICATIONS

Gene Maping and Gene Enrichment by the Avidin–Biotin Interaction: Use of Cytochrome–c as a Polyamine Bridge; Ann Sodja and Norman Davidson; Nucleic Acids Research, vol. 5, No. 2, Feb. 1978, pp. 385–401.

Enzymatic Synthesis of Biotin–labeled Polynucleotides: Novel Nucleic Acid Affinity Probes, Pennina R. Langer, Alex A. Waldrop and David C. Ward; Proc. Nat'l. Acad. Sci. USA, vol. 78, No. 11, pp. 6633–6637.

Ligation of Oligonucleotides to Nucleic Acids or Proteins via Disulfide Bonds, Barbara C. F. Chu and Leslie E. Orgel; Nucleic Acids Research, vol. 16, No. 9, 1988, pp. 3671–3691.

*Primary Examiner*—Scott W. Houtteman
*Attorney, Agent, or Firm*—Daryl Grzybicki; Hank Sartorio

[57] ABSTRACT

A method for detecting and isolating a target sequence in a sample of nucleic acids is provided using a bifunctional hybridization probe capable of hybridizing to the target sequence that includes a detectable marker and a first complexing agent capable of forming a binding pair with a second complexing agent. A kit is also provided for detecting a target sequence in a sample of nucleic acids using a bifunctional hybridization probe according to this method.

16 Claims, 5 Drawing Sheets

DETECT
DETECTABLE
MARKER

DETECT
DETECTABLE
MARKER

∫ = DETACHMENT POINT

DIGEST
IMMOBILIZED
NUCLEIC
ACIDS WITH
DNase

DETACH SECOND
COMPLEXING AGENT
FROM SOLID SUPPORT

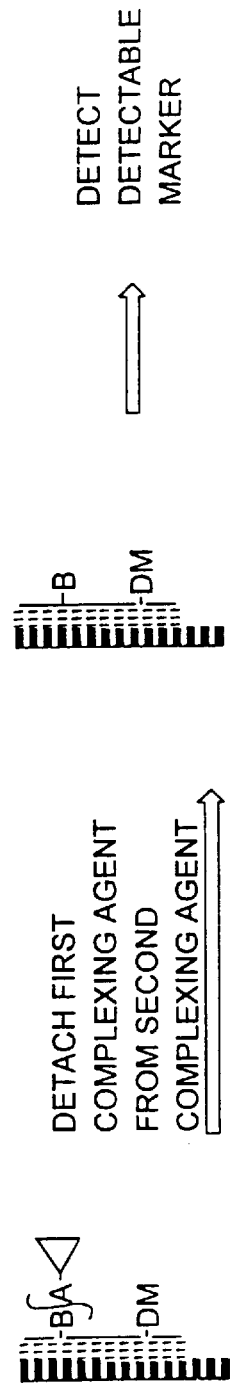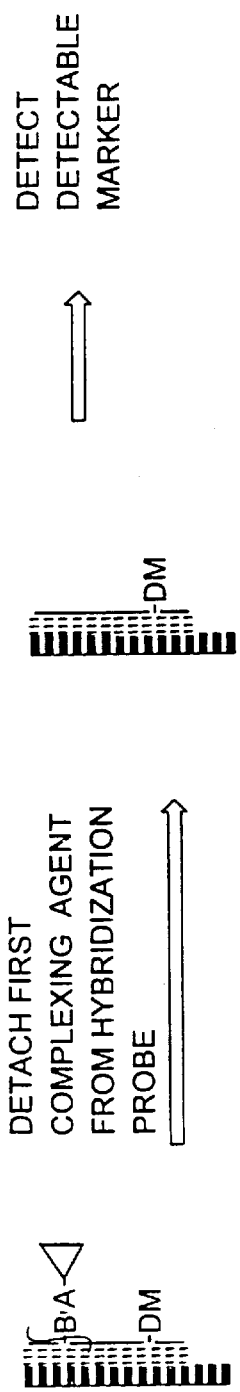

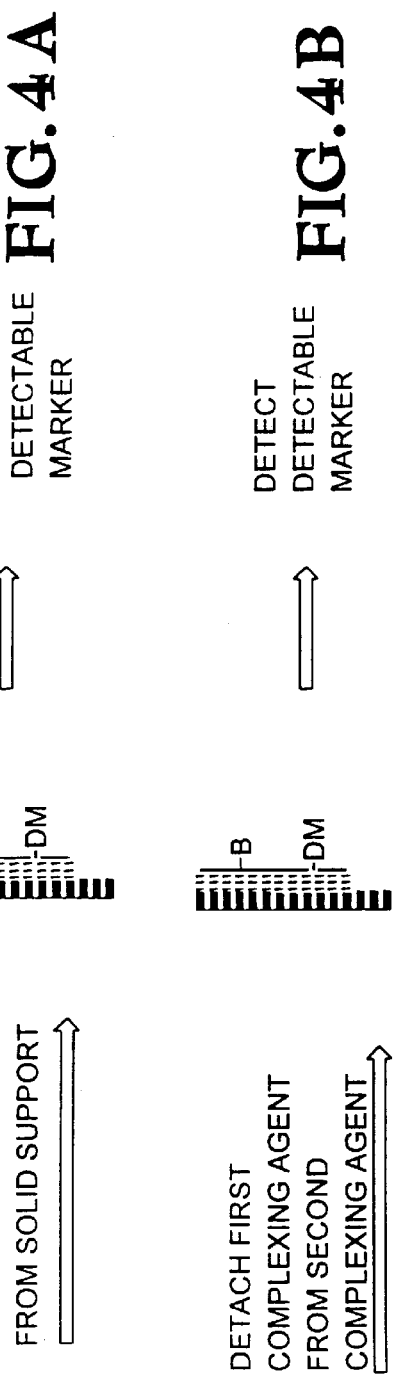

DETECTION AND ISOLATION OF NUCLEIC ACID SEQUENCES USING A BIFUNCTIONAL HYBRIDIZATION PROBE

The United States government has rights in this invention pursuant to Contract Number W-7405-ENG-48 between the United States Department of Energy and the University of California for the operation of Lawrence Livermore National Laboratory.

BACKGROUND OF THE INVENTION

1. Field of the Invention

The present invention relates to a method for identifying nucleic acid sequences using a hybridization probe with a detectable marker and a complexing agent for immobilizing the probe.

2. Description of Related Art

A variety of assays have been developed to detect the presence of a particular nucleic acid sequence, hereinafter referred to as a target sequence, through selective hybridization of a hybridization probe to the target sequence. In order for a hybridization probe to hybridize to a target sequence, the hybridization probe must contain a nucleic acid sequence that is at least partially complementary to the target sequence. The complementary sequence of the probe must also be sufficiently long so that the hybridization probe selectively hybridizes to the target sequence over non-target sequences.

In addition to hybridizing a hybridization probe to a target sequence, the hybridization probe must be detectable. A variety of sandwich hybridization assays have been developed which identify a target nucleic acid sequence through the hybridization of a target nucleic acid sequence to two different hybridization probes. The first step of the assay generally involves the hybridization of a target nucleic acid sequence to a first hybridization probe. The hybridized pair is then generally immobilized to a solid support. A second hybridization probe containing a detectable marker is then hybridized to either the target sequence or the first hybridization probe, thereby enabling the target sequence hybridized to the first hybridization probe to be detected.

Sandwich hybridization assays require the use of two different hybridization probes where each hybridization probe hybridizes to a separate, non-overlapping portion of the target nucleic acid sequence. However, it is not always possible to design two hybridization probes to a target sequence where each hybridization probe hybridizes to different non-overlapping portions of the target sequence. As a result, some prior art sandwich hybridization assays employ hybridization probes that are not specific for the target nucleic acid. This significantly limits the quantitative accuracy of the assay for detecting target nucleic acid sequences in a sample.

It is an object of the present invention to provide an efficient hybridization assay for the identification of target nucleic acid sequences using a hybridization probe with a detectable marker and a complexing agent for immobilizing the probe, both randomly attached to nucleic acids along the hybridization probe sequence.

SUMMARY OF THE INVENTION

A method for detecting and isolating a target sequence in a sample of nucleic acids is provided using a bifunctional hybridization probe which includes a detectable marker and a first complexing agent capable of forming a binding pair with a second complexing agent.

According to one embodiment of the method of the present invention, a sample of nucleic acids containing a target sequence is contacted under conditions favorable for hybridization with a bifunctional hybridization probe which is capable of hybridizing to the target sequence. Once the bifunctional hybridization probe has been hybridized to the target sequences in the nucleic acid sample, the nucleic acids are isolated from any nonhybridized bifunctional hybridization probe. This can be readily done based on size, preferably through gel electrophoresis.

The isolated nucleic acids, including those containing a target sequence to which a bifunctional hybridization probe is hybridized, are then contacted with a second complexing agent, the second complexing agent being attached to a solid support. The second complexing agent is selected such that it binds to the first complexing agent on the bifunctional hybridization probe to immobilize the probe on the solid support. Any target sequence in the nucleic acid sample which is hybridized to a bifunctional hybridization probe will also become immobilized on to the solid support. Since all nonhybridized bifunctional hybridization probes are removed in the prior isolation step, only bifunctional hybridization probes which are hybridized to a target sequence are immobilized.

The immobilized nucleic acids, i.e., those which contain a target sequence, are then isolated from any nonimmobilized nucleic acids, i.e., those which do not contain a target sequence. After this second isolation step, any target sequences in the remaining immobilized target nucleic acids are detected by detecting the detectable marker attached to the bifunctional hybridization probe.

In order to isolate the immobilized target sequences, the bifunctional hybridization probe is preferably detachably linked to the solid support. This may be accomplished by incorporating a detachable linker between the bifunctional hybridization probe and the first complexing agent, between the solid support and the second complexing agent or between the first and second complexing agents. The presence of the released target sequences may be determined by detecting the presence of the detectable marker on the bifunctional hybridization probe or by detecting the presence of the released target sequence itself.

When a detachable linker is employed, purification of the target nucleic acid sequence hybridized to the bifunctional probe can be accomplished by releasing the target nucleic acid sequences from the solid support, dehybridizing the target sequence and the bifunctional probe, and purifying the target sequence, for example by gel electrophoresis. Thus, using a detachable linker, the target sequence may readily be isolated and quantified.

In an alternate embodiment of the method, the bifunctional hybridization probe is immobilized before hybridization to the nucleic acid sample. When the bifunctional hybridization probe is immobilized prior to hybridization, it is preferred that the bifunctional hybridization probe be detachably linked to the solid support. According to this embodiment, the target sequences in the nucleic acid sample are immobilized by hybridization to the immobilized bifunctional hybridization probe. Once immobilized, the target sequences are then separated from any non-immobilized nucleic acids, leaving only the nucleic acids containing the target sequence immobilized on the solid support. The immobilized bifunctional hybridization probes, and the target sequence hybridized thereto, are then detached from the solid support. The target sequences that are released are then isolated from any nonhybridized bifunctional hybridization probe, for example by gel electrophoresis. The isolated target sequences may then be quantified by detecting the detectable marker which is attached to the target sequences through the hybridization of the bifunctional hybridization probe to the target sequences.

According to the present invention, the first complexing agent is preferably an antigen, antibody, biotin, a biotin derivative or analogue, avidin or an avidin derivative and analogue. The detectable marker is preferably a radioisotope, an isotope measurable by AMS, a fluorescent molecule, a chemiluminescent molecule, an antibody, the nucleic acid itself or an enzymatically modifiable substrate, the modified enzymatic substrate being analytically detectable.

A kit is also provided for detecting a target nucleic acid sequence in a sample. In one embodiment, the kit includes a bifunctional hybridization probe having a nucleic acid sequence capable of hybridizing to a target sequence. Attached to the bifunctional hybridization probe is a detectable marker and a first complexing agent capable of forming a binding pair with a second complexing agent. The first complexing agent may be detachably linked to the bifunctional hybridization probe. The kit may further include a second complexing agent attached to a solid support as well as instructions for using the kit. The second complexing agent may be detachably linked to the solid support.

The assay of the present invention may also be readily adapted for the diagnosis of disease, the occurrence of which is associated with and/or identifiable by the presence or absence of a target nucleic acid sequence. According to this embodiment of the invention, the bifunctional hybridization probe selectively hybridizes to a nucleic acid sequence associated with and/or characteristic of a disease. The present invention also relates to a kit for diagnosing disease using the embodiments of the hybridization assay of the present invention.

BRIEF DESCRIPTION OF THE DRAWINGS

FIGS. 3A–E depict several approaches for isolating and/or detecting the detectable marker on the bifunctional hybridization probe where the bifunctional hybridization probe is hybridized to the nucleic acid sample prior to immobilization of the bifunctional hybridization probe.

FIG. 3A illustrates a detectable marker being detected by first digesting the nucleic acids immobilized on the solid support using DNase.

FIG. 3B illustrates the detectable marker being separated from the solid support prior to detection of the detectable marker by detaching the second complexing agent from the solid support using a detachable linker.

FIG. 3C illustrates the detectable marker being separated from the solid support prior to detection of the detectable marker by detaching the first and second complexing agents using a detachable linker.

FIG. 3D illustrates the detectable marker being separated from the solid support prior to detection of the detectable marker by detaching the first complexing agent from the hybridization probes using a detachable linker.

FIG. 3E illustrates the detectable marker being separated from the solid support prior to detection of the detectable marker by detaching the detectable marker from the hybridization probes using a detachable linker.

FIGS. 4A–C depict several approaches for isolating and/or detecting the detectable marker on the bifunctional hybridization probe where the bifunctional hybridization probe is immobilized prior to being hybridized to the nucleic acid sample.

FIG. 4A illustrates the detectable marker being separated from the solid support prior to detection of the detectable marker by detaching the second complexing agent from the solid support using a detachable linker.

FIG. 4B illustrates the detectable marker being separated from the solid support prior to detection of the detectable marker by detaching the first and second complexing agents using a detachable linker.

FIG. 4C illustrates the detectable marker being separated from the solid support prior to detection of the detectable marker by detaching the first complexing agent from the hybridization probes using a detachable linker.

DETAILED DESCRIPTION OF THE INVENTION

Figure 1:
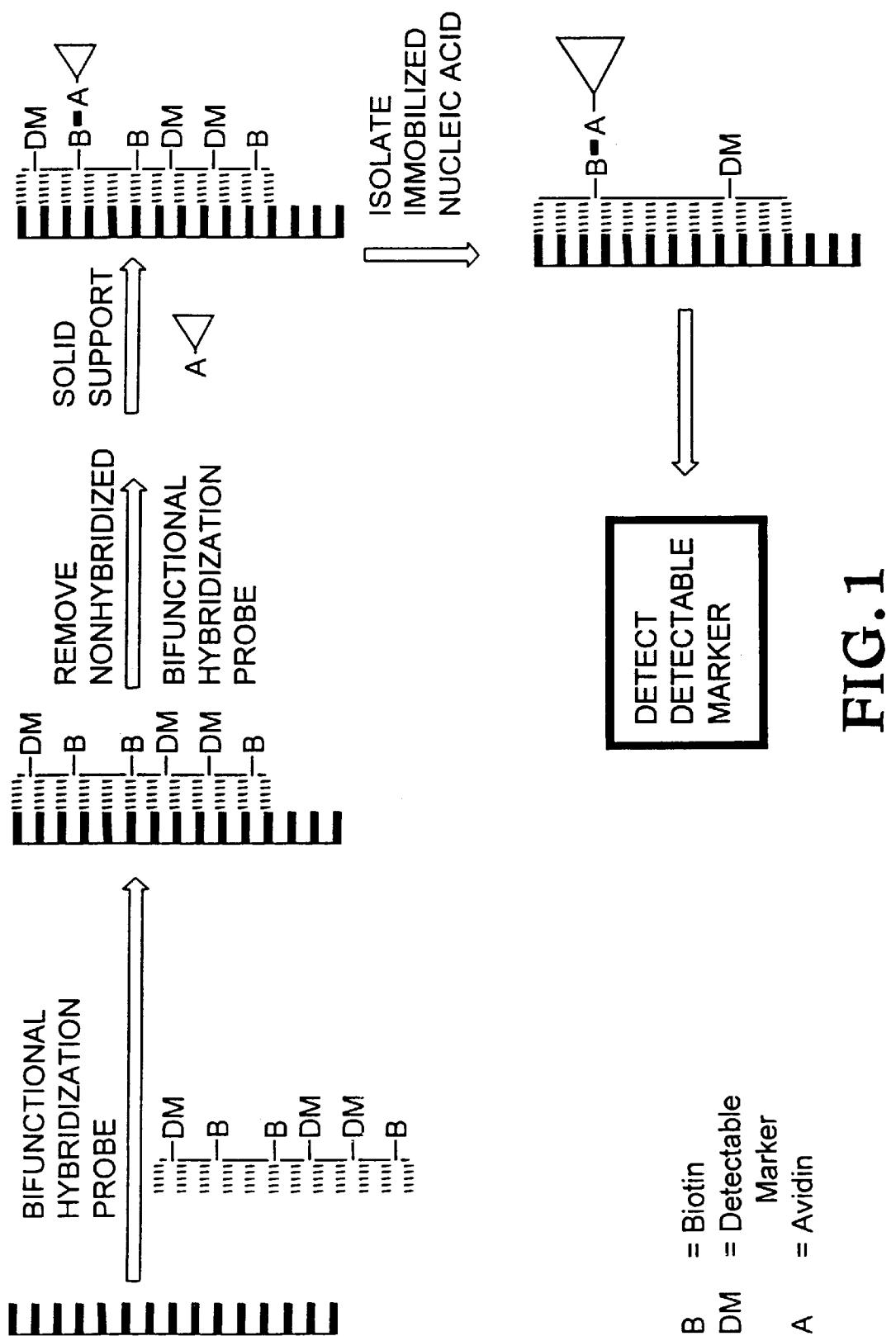
FIG. 1 schematically illustrates an embodiment of the hybridization assay of the present invention using a bifunctional hybridization probe in which the bifunctional hybridization probe is hybridized to a nucleic acid sample prior to immobilization of the bifunctional hybridization probe.

The present invention relates to a rapid and efficient hybridization assay for detecting, isolating, and accurately quantifying target sequences in a sample of nucleic acids. Nucleic acids, as the term is used herein, may be either DNA or RNA.

According to the method of the present invention, a bifunctional hybridization probe is used which hybridizes to a single sequence of a target nucleic acid. By designing the hybridization assay such that only one hybridization site on the target nucleic acid sequence is needed, the need for two separate hybridization probes, as is used in prior art sandwich hybridization assays, is eliminated. This greatly simplifies the complexity of the hybridization assay and makes it possible to assay for any target nucleic acid whose sequence is known.

According to the method of the present invention, the hybridization probe is bifunctional in that it includes both an immobilization agent and a detectable marker interspersed on the same probe. Fabrication of the bifunctional hybridization probe may be accomplished, for example, by nick translation, a well-known laboratory technique. The ability to produce the bifunctional probe by nick translation (which produces a bifunctional probe in one step during routine nick translation of an immobilization agent (e.g. biotin) into the target probe) eliminates the need to chemically attach a detectable marker DNA sequence to the target probe, as is used in prior art bifunctional probes. As a result, bifunctional probes may be prepared according to the present invention for any target sequence for which the nucleic acid sequence is known or for which the nucleic acid is available.

According to the present invention, the detectable marker is also introduced into the bifunctional probe by nick translation at the same time that the immobilization agent is introduced. This avoids the need to chemically attach a detectable marker to the hybridization probe which is difficult and requires extra steps. Further, the extra steps required to chemically introduce a detectable marker into a hybridization probe is necessary for the preparation of every different hybridization probe. Thus, introducing both an immobilizing agent and a detectable marker into the hybridization probe in a single step greatly simplifies the preparation of the bifunctional hybridization probes for a series of target sequences. As a result, the bifunctional hybridization probes may be produced with the same speed and ease that biotinylated probes are currently produced for sandwich hybridization assays employing two separate probes.

In a preferred embodiment, the hybridization assay is used to detect the presence or absence of a nucleic acid sequence associated with a disease. For example, the nucleic acid sequence to be detected may be a cancer gene or a pathogen (viral, fungal or bacterial) DNA insert.

According to the assay of the present invention, a sample of nucleic acids is first obtained. In applications where the nucleic acid sample consists of chromosomal DNA, the chromosomal DNA is first isolated from a sample of cells. Chromosomal DNA may be isolated by any of the variety of methods known in the art. For example, the chromosomal DNA may be isolated by the method taught in Vooijs, et al. Am. J. Hum. Genet. 52:586–597 (1993) or by using the GIBCO BRL TRIzol™ Reagent (Life Technologies, Gaithersburg, Md.), each of which is incorporated herein by reference.

Chromosomal DNA may be analyzed as whole chromosomes, chromosome fragments or chromosomal DNA fragments, all of which are hereinafter referred to as chromosomal DNA. The chromosomal DNA may be organized as an extended double strand, as extended nucleosomes, as chromatin fiber, as folded fiber, and as interphase, prophase or metaphase DNA. Sandberg, "The chromosomes in human cancer and leukemia", Elsevier; New York (1980), pp.69–73.

FIG. 1 schematically illustrates an embodiment of the hybridization assay of the present invention using a bifunctional hybridization probe in which the bifunctional hybridization probe is hybridized to the DNA sample prior to immobilization of the bifunctional hybridization probe. As illustrated in FIG. 1, a bifunctional hybridization probe is used which is capable of both immobilizing the target nucleic acid sequence and providing a mechanism for detecting the target nucleic acid sequence, i.e., the detection of a detectable marker attached to the bifunctional hybridization probe. The bifunctional hybridization probe includes a first complexing agent capable of forming a binding pair with a second complexing agent and a detectable marker.

Once the bifunctional hybridization probe has been hybridized to the target sequence in the nucleic acid sample, the sample of nucleic acids containing a target sequence is isolated from any excess, nonhybridized hybridization probe. This is most commonly done based on size, most preferably using gel electrophoresis. Two groups of nucleic acid sequences of different sizes are generally identified through gel electrophoresis, the larger sized nucleic acids including hybridized and nonhybridized DNA fragments, the smaller sized nucleic acids including the unhybridized bifunctional probe.

The band on the gel corresponding to the nucleic acid sample (based on size) may be analyzed for the presence of the detectable marker. If the group containing the larger sized nucleic acid fragments does not include the target sequence, the bifunctional probe will not hybridize to the DNA and hence will not be present in the group of larger sized nucleic acid fragments. As a result, no detectable marker will be detected in the group of larger sized fragments. Thus, when no detectable marker is detected in the group of larger sized nucleic acid fragments, one can conclude that no target sequences were present in the nucleic acid sample tested. However, if the detectable marker is detected, this indicates that the bifunctional hybridization probe has hybridized to a sequence in the sample, indicating the presence of the target sequence.

If the target sequence is determined to be present, the band including the target DNA is extracted from the gel and contacted with a second complexing agent, the second complexing agent being attached to a solid support such that when the first and second complexing agents are attached, target nucleic acids hybridized to the bifunctional hybridization probe become immobilized on to the solid support.

Once immobilized, the immobilized target sequences are isolated from any non-immobilized nucleic acids. Isolation of the immobilized nucleic acids from nonimmobilized nucleic acids may be accomplished by a variety of methods known in the art including, but not limited to, centrifugation, filtration, magnetic separation, chemical separation and washing.

After the immobilized target sequences have been isolated from any nonimmobilized nucleic acids, the immobilized sequences are analyzed for the presence of the detectable marker attached to the bifunctional hybridization probe. The quantity of a target sequence in a sample can then be readily determined by quantifying the detectable marker.

The hybridization probes used in the invention preferably are between about 100 and 1000 base pairs long. However, this probe length is not meant to be limiting. When it is desirable to use hybridization probes longer than 700 base pairs, and particularly when the probe is comparable in size to the target sequence, it is preferred that a bifunctional hybridization probe of the present invention is used. Other bifunctional hybridization probes which have a reporter molecule chemically attached to the immobilizing molecule will show a decreasing signal to target DNA ratio as the probe length increases. This is because the reporter group is a fixed size. In that case, the ratio of reporter molecule to probe size decreases with increasing probe size. In the present invention, the signal to target DNA ratio does not change with probe size because the reporter and immobilizing molecules are integrated directly along the length of the probe. Thus, in the present invention, the ratio of reporter molecules to immobilizing molecules is independent of the probe size.

In order to isolate the immobilized target nucleic acids, the bifunctional hybridization probe is preferably detachably linked to the solid support. This may be accomplished by incorporating a detachable linker between the bifunctional hybridization probe and the first complexing agent or by incorporating a detachable linker between the solid support and the second complexing agent. The presence of the released target nucleic acid sequences is determined by detecting the presence of the detectable marker on the bifunctional hybridization probe.

Figure 2:
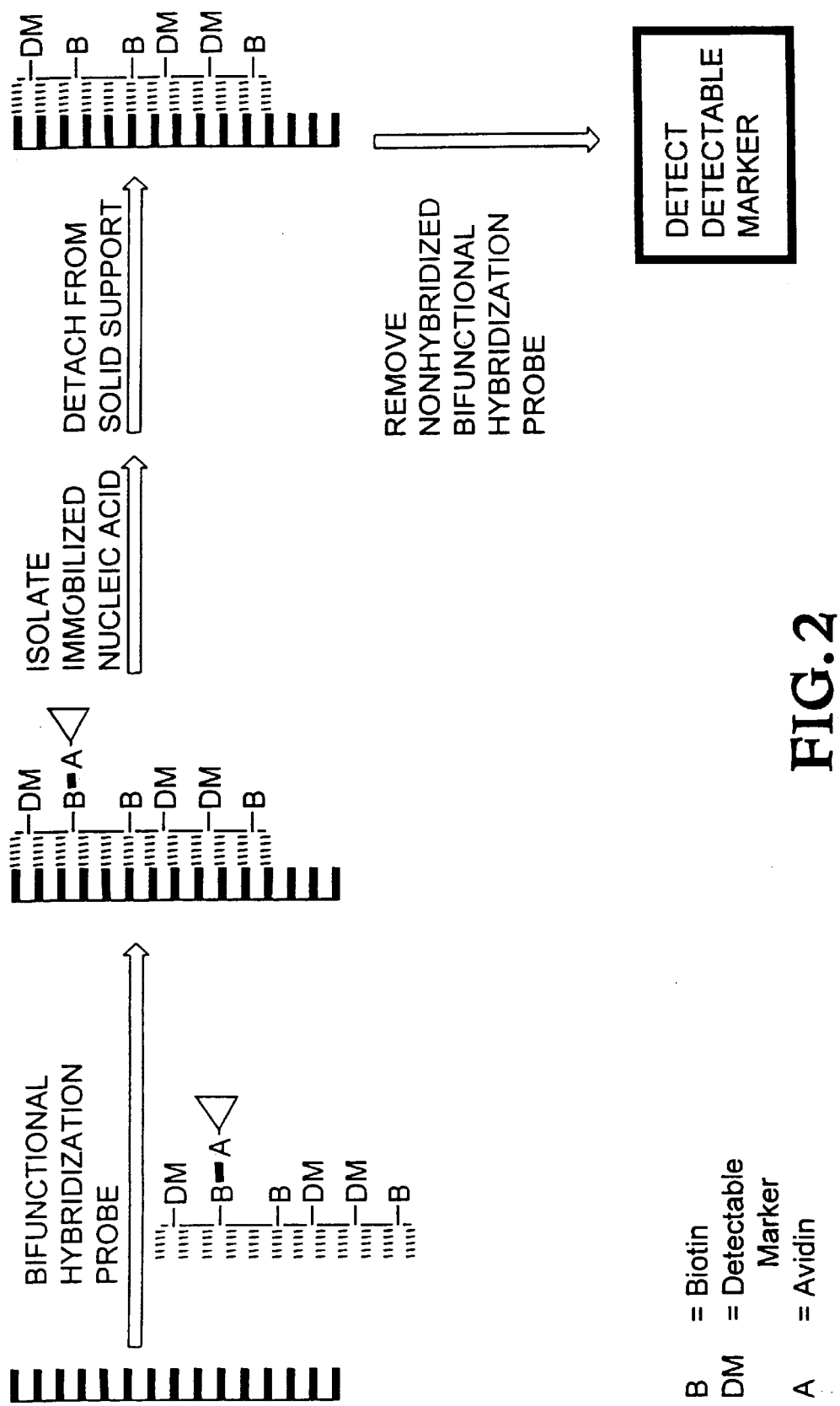
FIG. 2 schematically illustrates an embodiment of the hybridization assay of the present invention using a bifunctional hybridization probe in which the bifunctional hybridization probe is immobilized before being hybridized to the nucleic acid sample.

FIG. 2 schematically illustrates an embodiment of the hybridization assay of the present invention using a bifunctional hybridization probe in which the bifunctional hybridization probe is immobilized before being hybridized to the DNA sample. As illustrated in FIG. 2, the bifunctional hybridization probe is immobilized prior to hybridization by attachment of the second complexing agent to the first complexing agent. In this embodiment, it should be noted that the first and second complexing agents are preferably two reactive entities which form a detachable linkage.

When the bifunctional hybridization probe is immobilized prior to hybridization, the bifunctional hybridization probe is preferably detachably linked to the solid support as described above. According to this embodiment, the DNA sample is hybridized to the immobilized bifunctional hybridization probe. Once immobilized, the immobilized target sequences are separated from any non-immobilized nucleic acids leaving only the target DNA immobilized on the solid support. The immobilized bifunctional hybridization probes and the target sequence hybridized thereto are then detached from the solid support and purified, for example by gel electrophoresis and isolated from any nonhybridized bifunctional hybridization probes. Once isolated, the target sequences may be quantified by measuring the detectable marker attached to the bifunctional hybridization probe.

Regardless of whether the bifunctional hybridization probe is immobilized before or after hybridization to the DNA sample, when a detachable linker is employed, purification of the target nucleic acid sequence hybridized to the bifunctional probe can be accomplished by releasing the target nucleic acid sequences from the solid support followed by dehybridizing the target nucleic acid sequence from the bifunctional probe and purifying the target sequence, for example by gel electrophoresis. Thus, by using a detachable linker, the target nucleic acids may themselves be isolated. This provides a rapid and efficient route to the isolation and sequencing of the target nucleic acid.

The first and second complexing agents used in the present invention may be any pair of complexing agents which form a strong binding pair. Since elevated temperatures are generally required for hybridization, the binding pair should be stable at temperatures at least up to about 37° C. under hybridization conditions.

Examples of suitable binding pairs of complexing agents include antibody-antigen pairs, biotin-avidin and digoxigenin-anti-digoxigenin. Avidin-biotin and analogues and derivatives thereof are particularly preferred as binding pairs due to their enhanced thermal stability. Examples of avidin derivatives include, but are not limited to, streptavidin, succinyl avidin, ferritin avidin, enzyme avidin and crosslinked avidin. Examples of biotin derivatives include, but are not limited to caproylamidobiotin and biocytin. Examples of biotin analogues include, but are not limited to desthiobiotin and biotin sulfone. Biotin-antibiotin antibody is an example of a suitable antibody-antigen pair.

Any solid support to which a complexing agent may be attached may be used in the present invention. Examples of suitable solid support materials include, but are not limited to, silicates such as glass and silica gel, cellulose and nitrocellulose papers, nylon, polystyrene, polymethacrylate, latex, rubber, and fluorocarbon resins such as TEFLON™.

The solid support material may be used in a wide variety of shapes including, but not limited to slides and beads. Slides provide several functional advantages and thus are a preferred form of solid support. Slides can be readily used with any chromosome organization. Due to their flat surface, probe and hybridization reagents can be minimized using glass slides. Slides also enable the targeted application of reagents, are easy to keep at a constant temperature, are easy to wash and facilitate the direct visualization of RNA and/or DNA immobilized on the solid support. Removal of RNA and/or DNA immobilized on the solid support is also facilitated using slides. It is estimated that a standard microscope glass slide can contain 50,000 to 100,000 cells worth of DNA. Beads, such as BioMag Strepavidin magnetic beads are another preferred form of solid support containing a second complexing agent.

It is preferred that avidin or an avidin derivative be used as the second complexing agent. Avidin may be chemically attached to glass using the N-hydroxysuccinamide active ester of avidin as taught by Manning, et al. *Biochemistry* 16:1364–1370 (1977) and may be attached to nylon by a carbodiimide coupling as taught by Jasiewicz, et al. *Exp. Cell Res.* 100:213–217 (1976). Magnetic microbeads labelled with avidin and strepavidin labelled bead may be obtained from Advanced Magnetics, Inc., Cambridge, Mass. and from Spherotech, Inc., Libertyville, Ill.

Any analytically detectable marker that can be attached to or incorporated into a hybridization probe may be used in the present invention. An analytically detectable marker refers to any molecule, moiety or atom which can be analytically detected and quantified. Methods for detecting analytically detectable markers include, but are not limited to, radioactivity, fluorescence, absorbance, mass spectroscopy, EPR, NMR, XRF, luminescence and phosphorescence. For example, any radiolabel which provides an adequate signal and a sufficient half-life may be used as a detectable marker. Commonly used radioisotopes include $^3H$, $^{14}C$, $^{32}P$ and $^{125}I$. In a preferred embodiment, $^{14}C$ is used as the detectable marker and is detected by accelerator mass spectroscopy (AMS). $^{14}C$ is preferred because of its exceptionally long half-life and because of the very high sensitivity of AMS for detecting $^{14}C$ isotopes. Other isotopes that may be detected using AMS include, but are not limited to, $^3H$, $^{125}I$, $^{41}Ca$, $^{63}Ni$ and $^{36}C$.

Fluorescent molecules, such as fluorescein and its derivatives, rhodamine and its derivatives, dansyl, umbeliferone and acridimium, and chemiluminescent molecules such as luciferin and 2,3-dihydrophthalazinediones may also be used as detectable markers. Molecules which bind to an analytically detectable marker may also be covalently attached to or incorporated into hybridization probe, for example, as taught by Ward, European Patent Application No. 63,879 which is incorporated herein by reference. In such instances, the hybridization probe is detected by adding an analytically detectable marker which specifically binds to the probe, thereby enabling detection of the probe. Examples of such molecules and their analytically detectable counterparts include biotin and either fluorescent or chemiluminescent avidin. Antibodies that bind to an analytically detectable antigen may also be used as a detectable marker. The detectable marker may also be a molecule which, when subjected to chemical or enzymatic modification, becomes analytically detectable such as those disclosed in Leary, et al., *Proc. Natl. Acad. Sci. (U.S.A.)*, 80:4045–4049 (1983) which is incorporated herein by reference. Other examples of suitable detectable markers include protein binding sequences which can be detected by binding proteins, such as those disclosed in U.S. Pat. No. 4,556,643 which is incorporated herein by reference. As discussed herein, the nucleic acid sequence employed in the first and/or second hybridization probe may function as a detectable marker where the bases forming the nucleic acid sequence are quantified using techniques known in the art.

Once any nucleic acids and hybridization probes that are not immobilized to the solid support have been removed, the presence or absence of the detectable marker attached to the second fraction of hybridization probes is detected in order to quantify the target sequence. The detection and quantification of the detectable marker can be performed using a variety of methods, depending upon the particular hybridization probes and detectable markers employed.

FIGS. 3A–E depict several approaches for isolating and/or detecting the detectable marker on the bifunctional hybridization probe where the bifunctional hybridization probe is hybridized to the DNA sample prior to immobilization of the bifunctional hybridization probe. As illustrated in FIG. 3A, the detectable marker may be detected by treating the immobilized nucleic acid sequences with DNase to digest any DNA immobilized on the solid support. The digested DNA is then collected after enzymatic digestion and analyzed for the presence of the detectable marker. Alternatively, the nucleic acids attached to the solid support may be removed from the solid support by a variety of chemical and physical methods available, including, for example, treatment with a basic solution (e.g., concentrated NaOH), treatment with an acidic solution and denaturalization of DNA using standard methods such as elevated temperatures or reagents. For example, when the detectable marker used is $^{14}C$, the entire solid support containing the immobilized nucleic acids and hybridization probes may be graphitized and analyzed using accelerator mass spectroscopy (AMS). The use of AMS and a $^{14}C$ detectable marker to quantify the target sequence is described in greater detail in Example 1.

As illustrated in FIG. 3B, the detectable marker may be separated from the solid support prior to detection of the detectable marker by breaking a bond between the second complexing agent and the solid support. This may be accomplished through the use of a detachable linker positioned between the second complexing agent and the solid support. Examples of suitable detachable linkages include, but are not limited to the detachable linkers described in Lin, et al., *J. Org. Chem.* 56:6850–6856 (1991); Ph.D. Thesis of W. -C. Lin, U. C. Riverside, (1990); Hobart, et al., *J. Immunological Methods* 153: 93–98 (1992); Jayabaskaran, et al., *Preparative Biochemistry* 17(2): 121–141 (1987); Mouton, et al., *Archives of Biochemistry and Biophysics* 218: 101–108 (1982); Funkakoshi, et al., *J. of Chromatography* 638:21–27 (1993); Gildea, et al., *Tetrahedron Letters* 31: 7095–7098 (1990); WO 85/04674; and Dynabeads (Dynal, Inc., 5 Delaware Drive, Lake Success, N.Y. 11042), each of which are incorporated herein by reference.

As illustrated in FIG. 3C, the detectable marker may be separated from the solid support prior to detection of the detectable marker by breaking a bond between the first and second complexing agents. For example, using antidigoxigenin and digoxigenin as the first and second binding agents, a bond between the first and second complexing agents may be broken.

As illustrated in FIG. 3D, the detectable marker may be separated from the solid support prior to detection of the detectable marker by breaking the bond between the first complexing agent and the nucleic acid sequences forming the hybridization probe. This may be accomplished through the use of a detachable linker positioned between the first complexing agent and the nucleic acid sequence forming the hybridization probe. Examples of suitable detachable linkages include, but are not limited to the detachable linkers described in the references cited above.

As illustrated in FIG. 3E, the detectable marker may be separated from the solid support prior to detection by detaching the detectable marker from the hybridization probe. This may be accomplished through the use of a detachable linker between the detectable marker and the nucleic acid sequence forming the hybridization probe. Examples of suitable detachable linkages include, but are not limited to, the detachable linkers described in the references cited above.

The detectable marker may be detected by a variety of methods known in the art, depending on the particular detectable marker employed. For example, AMS may be used when the detectable marker is a radioisotope such as $^{14}C$, liquid scintillation may be used when the detectable marker is tritiated thymidine and standard fluorescence or spectroscopic methods may be used when the detectable marker is a fluorescent molecule or the DNA itself.

When the bifunctional hybridization probe is immobilized prior to hybridization, the immobilized bifunctional hybridization probes and the target sequence hybridized thereto may be detached from the solid support according to the schemes illustrated in FIGS. 4A–C.

As illustrated in FIG. 4A, the target sequence hybridized to the bifunctional probe may be separated from the solid support by breaking a bond between the second complexing agent and the solid support. This may be accomplished through the use of a detachable linker positioned between the second complexing agent and the solid support. Examples of suitable detachable linkages include, but are not limited to the detachable linkers described in Lin, et al., *J. Org. Chem.* 56:6850–6856 (1991); Ph.D. Thesis of W. -C. Lin, U. C. Riverside, (1990); Hobart, et al., *J. Immunological Methods* 153: 93–98 (1992); Jayabaskaran, et al., *Preparative Biochemistry* 17(2): 121–141 (1987); Mouton, et al., *Archives of Biochemistry and Biophysics* 218: 101–108 (1982); Funkakoshi, et al., *J. of Chromatography* 638:21–27 (1993); Gildea, et al., *Tetrahedron Letters* 31: 7095–7098 (1990); WO 85/04674; and Dynabeads (Dynal, Inc., 5 Delaware Drive, Lake Success, N.Y. 11042), each of which are incorporated herein by reference.

As illustrated in FIG. 4B, the target sequence hybridized to the bifunctional probe may be separated from the solid support by breaking a bond between the first and second complexing agents. For example, using antidigoxigenin and digoxigenin as the first and second binding agents, a bond between the first and second complexing agents may be broken.

As illustrated in FIG. 4C, the target sequence hybridized to the bifunctional probe may be separated from the solid support by breaking the bond between the first complexing agent and the nucleic acid sequences forming the hybridization probe. This may be accomplished through the use of a detachable linker positioned between the first complexing agent and the nucleic acid sequence forming the hybridization probe. Examples of suitable detachable linkages include, but are not limited to the detachable linkers described in the references cited above.

The quantity of the target nucleic acid sequence that is present may be determined based on the signal generated from the detectable marker using a calibration curve. The calibration curve may be formed by analyzing a serial dilution of a sample of nucleic acids having a known concentration of the target sequence. For example, a calibration curve may be generated by analyzing a series of known amounts of cells from a cell line in which the concentration of the target sequence is known. Alternatively, samples of cells may be analyzed according to the method of the present invention and according to a method known in the art for quantifying the target nucleic acid sequence. Alternative methods for generating a calibration curve are within the level of skill in the art and may be used in conjunction with the method of the present invention.

The present invention also relates to a kit for performing the hybridization assays of the present invention. Unless otherwise specified, the components of the kit are the same as those used in the assays of the present invention.

The kit includes a bifunctional hybridization probe including a nucleic acid sequence capable of hybridizing to a target sequence. Attached to the nucleic acid sequence is a first complexing agent capable of forming a binding pair with a second complexing agent and a detectable marker. Optionally, the kit may also include written instructions for practicing the assay and one or more target nucleic acid sequences for use in the preparation of a calibration curve.

The following examples set forth the method for detecting a nucleic acid sequence according to the present invention. Further objectives and advantages of the present invention other than those set forth above will become apparent from the examples which are not intended to limit the scope of the present invention.

EXAMPLE 1

Hybridization Assay Employing Bifunctional Hybridization Probe

According to the present invention, a target nucleic acid sequence is contacted with a bifunctional hybridization probe which can hybridize to the target sequence. The bifunctional hybridization probe includes biotin as the first complexing agent. The bifunctional hybridization probe also includes $^{14}C$ as the detectable marker.

Several techniques are known in the art for generating singled stranded hybridization probes to a target nucleic acid sequence, for example, as a messenger RNA sequence corresponding to the target sequence, or complementary DNA obtained from reverse transcriptase, or as genomic DNA obtained from the target genome by endonuclease digestion.

Biotinylating the hybridization probe may be accomplished by incorporating biotinylated uridine according to the method of Pinkel, et al., Proc. Natl. Acad. Sci. (USA) 83:2934–2938 (1986), which is incorporated herein by reference. Alternate methods for biotinylating the hybridization probe include nick translation, pcr, or an enzymatic methods using a BioPrim kit from GIBCO BRL.

$^{14}C$ labelling the hybridization probe may be accomplished by introducing a $^{14}C$ labelled nucleotide while the hybridization probe is being biotinylated by adding the $^{14}C$ labelled nucleotide to the reaction mixture. The proportion of the biotin to the detectable marker, in this case $^{14}C$, may be controlled by controlling the proportion of biotinylated uridine to $^{14}C$ labelled nucleotide employed.

Once the bifunctional hybridization probe has been prepared, the bifunctional hybridization probe is contacted with a sample of nucleic acids under conditions favorable for hybridization.

After hybridization to the sample of nucleic acids has been completed, any nonhybridized probes are separated from the sample of nucleic acids by gel electrophoresis. This is possible because the nucleic acids will generally be significantly larger in size than the probe. The nucleic acids in the gel band, which include the bifunctional probe hybridized thereto, are then isolated from the gel and added to a solid support labelled with avidin to immobilize any bifunctional hybridization probe present in the band by an avidin-biotin linkage. Any nucleic acids hybridized to the bifunctional hybridization probe will also become immobilized to the solid support. The avidin labelled solid support may be prepared by the methods described in Manning, et al. Biochemistry 16:1364–1370 (1977) and Jasiewicz, et al. Exp. Cell Res. 100:213–217 (1976), each of which are incorporated herein by reference.

The solid support is then washed with cold, pH 7 buffered saline to remove any nucleic acid segments which are not immobilized on the solid support. The nucleic acid segments removed in this step correspond to those nucleic acid segments which do not contain the target sequence since no hybridization probe has hybridized to them.

Once any non-immobilized nucleic acid segments have been removed by the saline wash, the nucleic acids immobilized on the solid support are analyzed for the presence of $^{14}C$. DNase or concentrated NaOH is employed to separate any immobilized nucleic acids from the solid support. The nucleic acids isolated are then grafitized and analyzed using AMS for the presence of $^{14}C$ according to the method of Vogel et. al., Anal. Chem. 11: 142–149 (1991) which is incorporated herein by reference.

The $^{14}C$ signal obtained from the accelerator mass spectrometer may be calibrated by either performing the assay using a sample of containing a known quantity of the target nucleic acid. Alternatively, the sample of nucleic acids being analyzed may be analyzed according to the method of the present invention and according to a method known in the art for quantifying the target nucleic acid. Then, by serially diluting the sample of nucleic acids and assaying the sample according to the method described in the present example, a calibration curve may be generated. Alternative methods for generating a calibration curve are within the level of skill in the art and may be used in conjunction with the method of the present invention.

EXAMPLE 2

Fluorescence Detection Of Bifunctional Hybridization Probe For Chromosome 4

A bifunctional probe for chromosome 4 was prepared by simultaneously nick translating a whole chromosome probe for chromosome 4 with 25% biotinylated trinucleotides and 75% digoxigenin. Biotin was detected on the dual labelled probe avidin-FITC which exhibits a green colored fluorescence. Digoxigenin was also detected on the same dual labelled probe by detecting the presence of digoxigenin using antidigoxigenin-Texas Red which exhibits a red colored fluorescence. The chromosome appeared yellow due to the presence of biotin.

While the present invention is disclosed by reference to the preferred embodiments and example detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method for detecting a target sequence in a sample of nucleic acids comprising:

hybridizing the target sequence with a hybridization probe, the hybridization probe including a nucleic acid sequence capable of hybridizing to the target sequence, a plurality of detectable markers, and a plurality of first complexing agents which are distinct from the detectable markers and which are capable of forming a binding pair with a second complexing agent;

isolating the sample of nucleic acids including any hybridization probe hybridized to the target sequence from any nonhybridized hybridization probe;

immobilizing the hybridized hybridization probe and the target sequence hybridized thereto by binding the first complexing agent attached to the hybridized hybridization probe to a second complexing agent attached to the solid support;

isolating the immobilized target sequence from any non-immobilized nucleic acids; and detecting the immobilized target sequence by detecting the detectable marker on the hybridized hybridization probe.

2. The method according to claim 1 wherein the first complexing agent is selected from the group consisting of antigens, antibodies, biotin, biotin derivatives and analogues, avidin and avidin derivatives and analogues.

3. The method according to claim 1 wherein the detectable marker is selected from the group consisting of a radioisotope, a fluorescent molecule, a chemiluminescent molecule, an antibody and an enzymatically modifiable substrate, the modified enzymatic substrate being analytically detectable.

4. The method according to claim 1 wherein the detectable marker is $^{14}C$ and the step of detecting the immobilized nucleic acids containing the target sequence includes detecting the $^{14}C$ detectable marker by accelerator mass spectroscopy.

5. The method according to claim 1 wherein the bond between the first and second complexing agents is detachable, the step of detecting the detectable marker including:

detaching the first and second complexing agents to release the detectable marker from the solid support; and detecting the detectable marker released from the solid support.

6. The method according to claim 1 wherein the bond between the first complexing agent and the hybridization probe is detachable, the step of detecting the detectable marker including:

detaching the first complexing agent from the hybridization probe to release the detectable marker from the solid support; and detecting the detectable marker released from the solid support.

7. The method according to claim 1 wherein the bond between the detectable marker and the hybridization probe is detachable, the step of detecting the detectable marker including:

detaching the detectable marker from the hybridization probe to release the detectable marker from the solid support; and detecting the detectable marker released from the solid support.

8. A method for detecting a target sequence in a sample of nucleic acids comprising:

hybridizing the target sequence with a hybridization probe detachably immobilized on a solid support, the hybridization probe including a nucleic acid sequence capable of hybridizing to the target sequence, a plurality of detectable markers, a plurality of first complexing agents which are distinct from the detectable markers, the hybridization probe being immobilized on the solid support by a second complexing agent which is bound to the solid support and bound to the first complexing agent, hybridization causing the target sequence to be immobilized on the solid support;

isolating the immobilized target sequence from any non-immobilized nucleic acids;

detaching the immobilized target sequence from the solid support by detaching the hybridization probe from the solid support;

isolating any hybridization probe hybridized to the target sequence from any nonhybridized hybridization probe; and detecting the detectable marker attached to the hybridization probe hybridized to the target sequence.

9. The method according to claim 8 wherein the first complexing agent is selected from the group consisting of antigens, antibodies, biotin, biotin derivatives and analogues, avidin and avidin derivatives and analogues.

10. The method according to claim 8 wherein the detectable marker is selected from the group consisting of a radioisotope, a fluorescent molecule, a chemiluminescent molecule, an antibody and an enzymatically modifiable substrate, the modified enzymatic substrate being analytically detectable.

11. The method according to claim 8 wherein the detectable marker is $^{14}C$ and the step of detecting the immobilized nucleic acids containing the target sequence includes detecting the $^{14}C$ detectable marker by accelerator mass spectroscopy.

12. The method according to claim 8 wherein the bond between the first and second complexing agents is detachable, the step of detecting the detectable marker including:

detaching the first and second complexing agents to release the detectable marker from the solid support; and detecting the detectable marker released from the solid support.

13. The method according to claim 8 wherein the bond between the first complexing agent and the hybridization probe is detachable, the step of detecting the detectable marker including:

detaching the first complexing agent from the hybridization probe to release the detectable marker from the solid support; and detecting the detectable marker released from the solid support.

14. The method according to claim 8 wherein the bond between the detectable marker and the hybridization probe is detachable, the step of detecting the detectable marker including:

detaching the detectable marker from the hybridization probe to release the detectable marker from the solid support; and detecting the detectable marker released from the solid support.

15. The method of claim 1 wherein the bifunctional hybridization probe is at least 700 bp long.

16. The method of claim 8 wherein the hybridization probe is at least 700 bp long.

* * * * *